United States Patent [19]
Davis et al.

[11] Patent Number: 6,072,041
[45] Date of Patent: Jun. 6, 2000

[54] FUSION PROTEINS FOR PROTEIN DELIVERY

[75] Inventors: Pamela B. Davis, Cleveland Heights; Thomas Ferkol, Concord, both of Ohio; Elizabeth Eckman, Ponte Vedra Beach, Fla.; John Schreiber, Gates Mills, Ohio; John M. Luk, South Horizons, The Hong Kong Special Administrative Region of the People's Republic of China

[73] Assignee: Case Western Reserve University, Cleveland, Ohio

[21] Appl. No.: 08/957,333

[22] Filed: Oct. 24, 1997

Related U.S. Application Data

[63] Continuation-in-part of application No. 08/655,705, Jun. 3, 1996, and application No. 08/656,906, Jun. 3, 1996.

[51] Int. Cl.[7] .............................. C07K 1/00; C07K 16/00; A61K 38/00; C07H 21/02
[52] U.S. Cl. ........................... 530/866; 514/12; 536/23.1; 530/867; 530/402; 530/391.1; 530/391.7
[58] Field of Search .................................. 530/402, 866, 530/867, 391.1, 391.7; 514/12; 536/23.1

[56] References Cited

U.S. PATENT DOCUMENTS 5,108,921  4/1992  Low et al. ............................ 435/240.1

OTHER PUBLICATIONS

Elizabeth Eckman et al., Pediatric Pulmonology 14 (Suppl.): A229 "Targeting the Polymeric Immunoglobulin Receptor as a Means of Directing Therapeutic Proteins to the Airway", 1997.

Elizabeth Eckman et al., Pediatridic Pulmonology 13 (Suppl.) A242 "Structure and Function of Anti–Human Secretory Component FV/Human Alpha 1–Antitrypsin Fusion Proteins", 1997.

Ernst Wagner et al. "Transferrin–polycation–DNA complexes: The effect of polycations on the structure of the complex and DNA delivery to cells" Proc. Natl. Acad. Sci. USA vol. 88, pp. 4255–4259, May 1991.

*Primary Examiner*—Hankyel Park
*Attorney, Agent, or Firm*—Banner & Witcoff, Ltd.

[57] ABSTRACT

A protein conjugate consisting of antibody directed at the pIgR and $A_1AT$ can be transported specifically from the basolateral surface of epithelial cells to the apical surface. This approach provides us with the ability to deliver a therapeutic protein directly to the apical surface of the epithelium, by targeting the pIgR with an appropriate ligand. Thus, the highest concentration of the antiprotease will be at the apical surface, where it can do the greatest good in accelerating the inflammatory response.

11 Claims, 12 Drawing Sheets

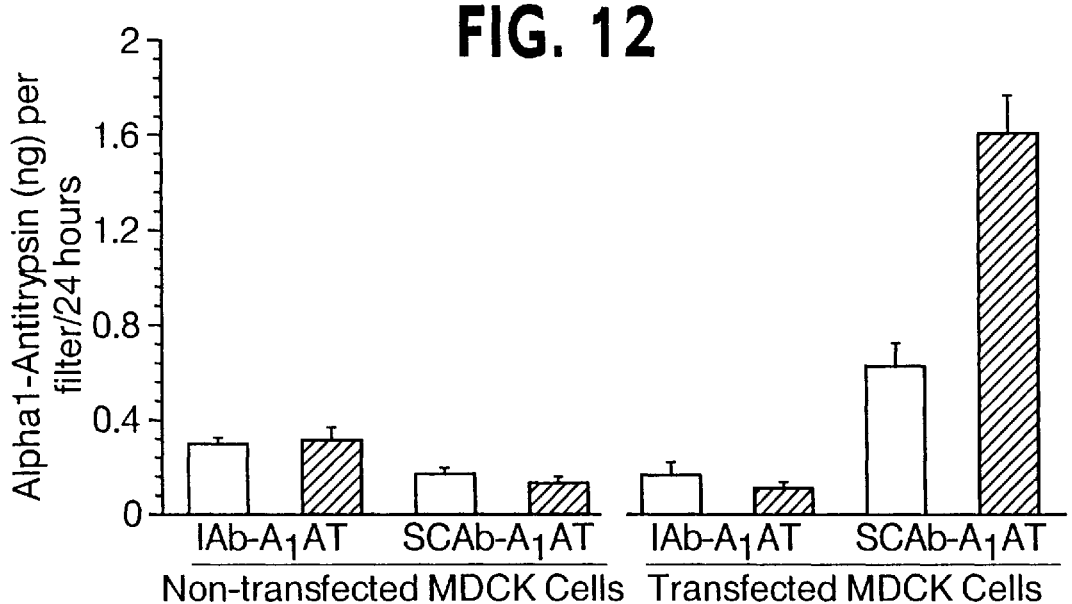
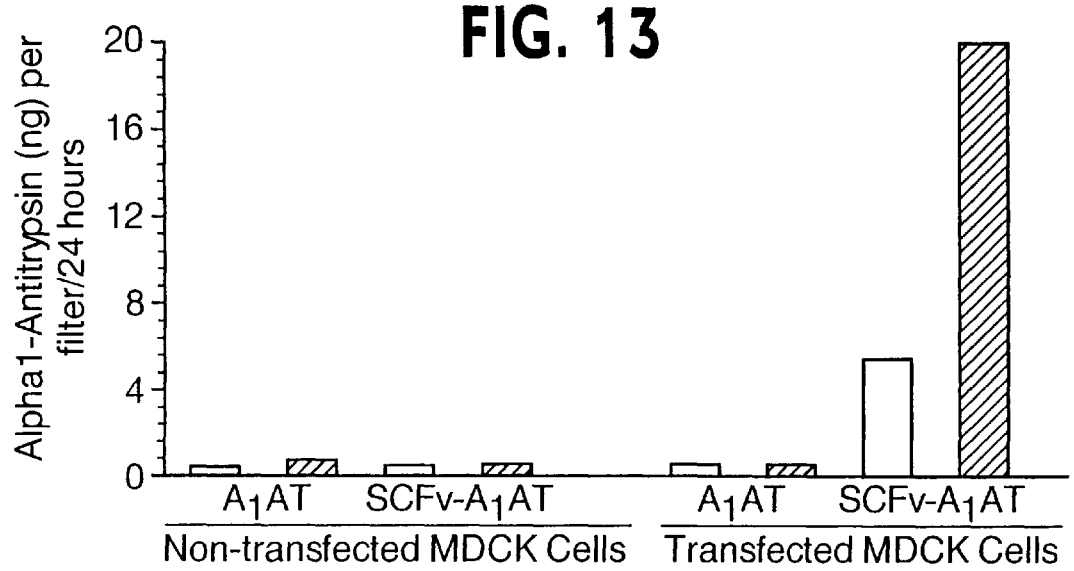

6,072,041

FUSION PROTEINS FOR PROTEIN DELIVERY

This application is a continuation-in-part of U.S. Ser. No. 08/655,705 filed Jun. 3, 1996, and 08/656,906 filed Jun. 3, 1996, the disclosures of which are expressly incorporated herein by reference.

This invention was made with government support under DK49138, DK27651, and DK43999 awarded by the National Institute of Health. The government has certain rights in the invention.

BACKGROUND OF THE INVENTION

The epithelium is the first line of defense of the airways against invading pathogens. Many of the non-specific defenses against such invaders arise from respiratory epithelial cells. Epithelial cells produce low molecular weight antimicrobial peptides, antibacterial enzymes, and antiproteases. In addition, secretory immunoglobulin A, a non-specific immunoglobulin defense, is trafficked into the airway via a specialized receptor, the polymeric immunoglobulin receptor (pIgR), that is expressed only on epithelial cells.

These epithelial defenses are breached early in the life of patients with cystic fibrosis (CF). Once live bacteria reach their surface, the epithelial cells direct the initial inflammatory response by releasing interleukin-8 (IL-8) and interleukin-6 (IL6) as well as reducing expression of interleukin-10 (IL-10). The chemoattractants, combined with increased expression of adhesin molecules for neutrophils, enhance inflammatory cell migration into the airways. Once there, the neutrophils, in an attempt to clear the bacteria, release lytic enzymes in the process. If the neutrophils remain adherent to the epithelium, these enzymes are released right at the epithelial surface. Both mechanical disruption of cells and even low concentrations of neutrophil elastase (NE) result in the greater release of pro-inflammatory mediators from the respiratory epithelium. Thus, the inflammatory response is further enhanced.

Several strategies to interrupt this cycle have been proposed. Augmenting the antibacterial defenses of the airway at the epithelial surface may be useful. Prevention of the escalation of the inflammatory responses engendered by the neutrophils migrating into the airway could be accomplished by preventing the action of elastase at the airway cell surface. Both antibiotics and antiproteases are available for clinical use. Unfortunately, the results of clinical studies examining the use of the antiprotease in patients with CF have been disappointing. The systemic administration of alpha$_1$-antitrypsin (A$_1$AT) is inefficient, and the levels achieved by the intravenous administration of the antiprotease are insufficient to inhibit the overwhelming amount NE in the lung of patients with CF. Aerosolized A$_1$AT should permit the direct delivery to the airways, but the antiprotease delivered by nebulization has been uneven and deposits the drug atop the mucus blanket rather than the critical site at the surface of the cell.

Thus there is a need in the art for methods to circumvent these difficulties and protect the respiratory epithelial cell surface.

SUMMARY OF THE INVENTION

It is an object of the invention to provide a fusion protein useful for protein delivery.

It is another object of the invention to provide a method of delivering a therapeutic protein to an epithelial cell.

It is yet another object of the invention to provide a nucleic acid molecule which encodes a fusion protein useful for protein delivery.

These and other objects of the invention are provided by one or more embodiments as described below. In one embodiment a fusion protein is provided. The fusion protein comprises a single chain Fv molecule directed against a human transcytotic receptor covalently linked to a therapeutic protein. The therapeutic protein may be, for example, $\alpha_1$-antitrypsin, a cytokine, such as interleukin-2 or interleukin-10, or a peptide antibiotic. Suitable peptide antibiotics include aerosporin, amphomycin, aspartocin, bacitracins, caperomycins, colistins, dactinomycins, glumamycins, gramicidin D, gramicidin S, mikamycin B, polymixins, pristinamycin, siomycin, staphylomycin S, thiostrepton, tyrocidines, tyrothricin, valinomycin, vancomycin, veramycin B. Any therapeutic protein which one wants delivered to epithelial cells may be used. The fusion protein may further comprise a linker region of less than 50, 40, 30, 20, or 10 amino acid residues. The linker can be covalently linked to and between the single chain Fv molecule and the therapeutic protein.

Also provided according to another aspect of the invention is a method of delivering a therapeutic protein to an epithelial cell. The method comprises: administering a fusion protein as described above to a patient, whereby the therapeutic protein is delivered to an epithelial cell. The eptithelial cell may be an airway epithelial cell or an intestinal lumen cell, for example. The liver may also be targeted. The administration mode may be any known in the art. However, intravenous administration has been found to be both convenient and efficient.

Nucleic acid molecules are also provided by the present invention. These encode a fusion protein comprising a single chain Fv molecule directed against a transcytotic receptor covalently linked to a therapeutic protein. The therapeutic protein may be, for example, $\alpha_1$-antitrypsin, a cytokine, such as interleukin-2 or interleukin-10, or a peptide antibiotic. Any therapeutic protein which one wants delivered to epithelial cells may be used. The fusion protein may further comprise a linker region of less than 50, 40, 30, 20, or 10 amino acid residues. The linker can be covalently linked to and between the single chain Fv molecule and the therapeutic protein. Host cells and vectors for replicating the nucleic acid molecules and for expressing the encoded fusion proteins are also provided. Any vectors or host cells may be used, whether prokaryotic or eukaryotic. Many vectors and host cells are known in the art for such purposes. It is well within the skill of the art to select an appropriate set for the desired application.

The present invention thus provides an efficient means of delivering therapeutic proteins to body parts which are often inaccessible or difficult to reliably access.

BRIEF DESCRIPTION OF THE DRAWINGS

FIG. 1. Schematic diagrams showing the transport of fusion proteins from the systemic circulation to the epithelial surface (Left). The fusion protein is bound to pIgR at the basolateral surface and is trafficked to the apical membrane (Center). Once it reaches the this surface, the fusion is released into the airway lumen, attached to secretory component of the polymeric immunoglobin receptor (SC), where the antiprotease component binds and neutralizes elastase (Right).

FIG. 2. Clearance and hepatic uptake of the anti-rat SC Fab. Blood (FIG. 2A) and bile (FIG. 2B) were collected every 10 minutes after injection with 50 µg of irrelevant (n=5) or anti-rat SC Fab (n=5), and analyzed for rabbit-derived antibodies using an ELISA. The Fab levels are represented as the percentage of peak serum concentrations.

FIG. 3. Schematic diagram of antibodies, Fab fragments, and single chain Fv fragments, showing the variable ($V_L$ and $V_H$ and constant ($C_L$ and $C_H$) regions. The antibody can also be resurfaced to replace the murine-specific framework regions in the Fv portion of the antibody with human sequences, which should further reduce its potential immunogenicity.

FIG. 4. Binding of anti-human SC monoclonal antibodies. (left) Relative binding of antibodies to purified human SC, as measured by ELISA. Monoclonal antibody 4121 indicated by solid column. (center) Relative binding of antibodies to sIgA. (right) Additional characterization of anti-human SC antibody 4121. Note the difference in affinity of the antibody to human and rat SC.

FIG. 5. (FIG. 5a) Construction of the anti-hSC Fv protein by PCR. Total cellular RNA was extracted from the antibody-producing cells and treated with Moloney Murine Leukemia Virus reverse transcriptase using random hexamers as primers. The resultant cDNA were screened for the $V_L$ and $V_H$ domains using different oligonucleotide primers, and these sequences were amplified by the PCR. The $V_L$ and $V_H$ domains were then amplified to include linker sequences that permitted splicing using a PCR technique called overlap extension to produce the full-length gene encoding the single chain Fv. (FIG. 5b) Schematic diagram of the structure of the anti-human SC Fv/human $A_1AT$ chimeric genes. (FIG. 5c) Restriction endonuclease digestion of plasmids containing the anti-human SC Fv/human $A_1AT$ chimeric gene. One microgram of plasmid DNA was digested with Cla I/Hind III (lane 1), Cla I/Xba I (lane 2), and Hind III (lane 3). Molecular weight markers are indicated in the right lane.

FIG. 6. In vitro transcription and translation of the anti-human SC Fv, human $A_1AT$, and anti-human SC Fv/human $A_1AT$ fusion proteins. Messenger RNA was translated using reticulate lysates, and [$^{35}$S]-labeled methionine was incorporated in the synthesized proteins. Analysis of the proteins by electrophoresis in SDS-polyacrylamide gels showed the presence of anti-human SC Fv, 26 kDa; human $A_1AT$, 52 kDa; and anti-human SC Fv/human $A_1AT$, 78 kDa.

FIG. 7. Expression of anti-human SC Fv/human $A_1AT$ and anti-D8 Fv/human $A_1AT$ in prokaryotes. Protein extracts from bacterial clones obtained after transformation were purified by nickel-chelate affinity chromatography, subjected to electrophoresis in SDS-polyacrylamide gels, and transferred onto nitrocellulose membrane filters using established methods. The polyhistidine, single chain Fv, and human $A_1AT$ components were each identified by Western blot hybridization. The following samples were examined: anti-D8 Fv/human $A_1AT$ (IR), and anti-human SC Fv/human $A_1AT$ (SC). Arrow shows the expected molecular weight of the fusion. A lower molecular weight band was also present, most likely representing truncated fusion protein.

FIG. 8. Recognition of human SC by the anti-human SC Fv/human $A_1AT$, as measured by ELISA. The anti-human SC Fv-based fusion proteins (SC) bound to SC from human milk, indicating that the Fv portion is functional. Fusion proteins containing the irrelevant, anti-D8 Fv (IR) did not bind to human SC.

FIG. 9. Expression of the human pIgR in transfected MDCK cells from the initial sort after selection for neomycin resistance and after serial sortings by fluorescent activated cell sorter analysis. Clones with the highest level of the pIgR expression were selected and used in subsequent experiments.

FIG. 10. (a) Schematic diagram of the cell model system, showing the transport of fusion proteins or antibodies across polarized MDCK cells expressing the pIgR in the basolateral-to-apical direction. (b) Transport of the anti-human SC antibodies across the MDCK cell monolayer that express the pIgR. Apical media was collected over six hours after addition of the antibodies to the basolateral media, and the concentration (ng/ml) of the mouse-derived antibody was determined by ELISA. The anti-human SC antibodies (4121 and 4214) were effectively transported from the basolateral surface to the apical media, whereas an irrelevant antibody (D8) did not. None of the antibodies were transported in the apical-to-basolateral direction.

FIG. 11. Effect of nocodazole and leupeptin on transport of antibodies across transduced MDCK cells. Apical media was collected at different times after addition of the monoclonal antibody (4121) to the basolateral media, and the concentration (ng/ml) of the mouse-derived antibody was determined by ELISA. Both leupeptin and nocodazole reduced the amount of antibody detected in the apical medium in a dose-dependent fashion. Moreover, no transport of the antibody occurred in nontransfected MDCK cells or transduced cells in the apical-to-basolateral direction.

FIG. 12. Transport of anti-human SC-based protein conjugates across a cell monolayer. Twenty-four hours after addition of 1 µg of the conjugate to the basolateral or apical media, media was collected from the apical or basolateral compartments, respectively. The amount of immunoreactive $A_1AT$ (ng) transported was determined by ELISA. The anti-human SC/human $A_1AT$ conjugate was effectively transported in the basolateral-to-apical direction (solid columns) across the MDCK cells that express the pIgR. Virtually no transcytosis of the fusion proteins occurred in the opposite, apical-to-basolateral direction (open columns). Nontransfected MDCK cells did not transport either the bona fide or irrelevant fusion protein (in each group, n=5).

FIG. 13. Transport of fusion proteins across a cell monolayer. Twenty-four hours after addition of 2 µg of the fusions to the basolateral or apical media, media was collected from the apical or basolateral compartments, respectively, and the amount of immunoreactive $A_1AT$ (ng) transported was measured by ELISA. The anti-human SC Fv/human $A_1AT$ fusion was effectively transported in the basolateral-to-apical direction (solid columns) across the MDCK cells that express the pIgR.

Considerably less of the fusion protein (approximately 25%) was transcytosed in the opposite, apical-to-basolateral direction (open columns). Purified human $A_1AT$ was not transported in either direction. Nontransfected MDCK cells did not transport either human $A_1AT$ or the fusion protein (in each group, n=5).

DETAILED DESCRIPTION OF THE INVENTION

Figure 1:
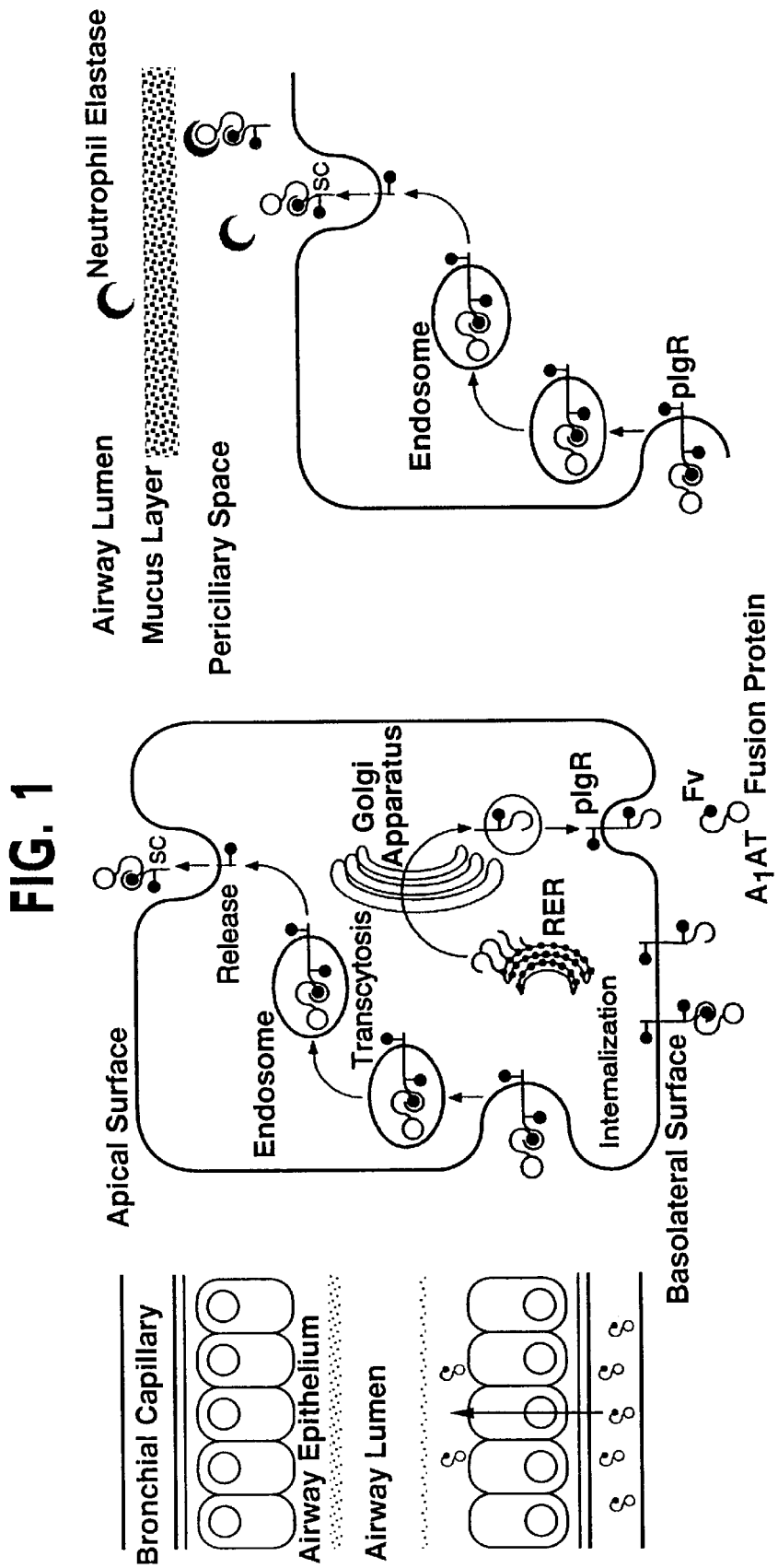

The inventors have discovered that one can efficiently deliver functional proteins to relatively inaccessible sites by targeting the respiratory epithelium via the polymeric immunoglobin receptor (pIgR). Once synthesized, the pIgR is trafficked to the basolateral surface of epithelial cells where it is specifically adapted for the internalization and nondegradative transfer of polymeric antibodies (21), i.e., dimeric immunoglobulin A (dIgA) and pentameric immunoglobulin M (pIgM). Once internalized, the receptor-ligand complex is transported across the cell to the apical surface, where the receptor is cleaved, releasing dIgA bound to the ectoplasmic domain of the receptor, or secretory component (SC), into the lumen (FIG. 1). The receptor does not require the natural ligand for endocytosis, and antibodies (or Fab fragments) directed against human SC also undergo efficient transcytosis (22). In humans, the receptor is expressed in airway epithelial cells which reach the luminal surface and in cells of the submucosal glands, especially serous cells (23). Thus, the pIgR in humans is well-suited for the delivery of fusion proteins to bronchi and bronchioles. Indeed, this receptor permits the delivery of the therapeutic proteins, such as antiprotease, to the apical surface of the respiratory epithelium.

The Fv portion of an antibody is a 26 kDa heterodimer consisting of the amino-terminal variable domains of the heavy and light chains, and is the smallest fragment to bear the antigen binding site (26). Genetically engineered single chain Fv (Fv) peptides have been synthesized by attaching the carboxyl terminus of one variable domain to the amino terminus of the other with a peptide linker (27–29). These Fv fragments have been shown to bind specific antigens, like the transferrin receptor (30), have been used to localize fusion proteins to targeted cells. Investigators have used such chimeras the deliver fusion proteins containing recombinant toxins (e.g., *Pseudomonas exotoxin*) and selectively kill cells in vitro and in vivo that express the appropriate receptor (30,31). There is considerable experience with expressing such fusions and retaining function of both components. Different Fv fragments can be employed to target different receptors, permitting the targeting of alternative cells. For example, cancer cells have receptors which can be used to target toxins to cancer cells. One example of such a receptor is EGFRvIII. See U.S. Pat. No. 5,212,290, which discloses antibodies to such a cancer cell specific receptor. Another useful receptor which can be targeted is the serpin-enzyme complex (sec) receptor. This receptor is found on macrophages. Targeting the sec receptor would allow the delivery, e.g., of anti-tuberculous antibiotics into macrophages, where tubercle bacilli reside. Preferably the receptor will be a transcytotic receptor, which can deliver the therapeutic fusion protein to the other side of a cell. Such receptors include the immunoglobulin transporting receptors in the gut of infants, and the immunoglobulin transporting receptors in the placenta.

A variety of functional proteins can be preferentially delivered to the respiratory epithelial surface. These include $A_1AT$ and SLPl. For example, if *Pseudomonas aeruginosa* interacts with respiratory epithelial cells to stimulate the production of IL-8 and other pro-inflammatory mediators, then it may be crucial that antibacterial protection occurs right at the epithelial surface. Recombinant defensins or protegrins, endogenous antibacterial peptides, could also be delivered to the periciliary space using such a bifunctional protein. Indeed, such proteins have been identified in human airway epithelial cells (8,9). The function of certain defensins against *Pseudomonas aeruginosa* may be hindered by the altered electrolyte composition of ELF in the CF lung (32). Thus, salt-insensitive forms of these antibacterial peptidesmay be used if the sodium chloride concentration of the ELF is abnormal. Another intriguing strategy is coupling Colistin, an agent already in use to treat pulmonary infections in patients with CF, to anti-human SC Fv (33). Killing Pseudomonas at the epithelial surface may be of value if it is the interaction of the bacteria and epithelial cell that incites the inflammatory process. Anti-inflammatory cytokines can also be transported to the epithelial surface in this manner (34) and pulmonary inflammation can be blocked by the specific delivery of interleukin-10 (IL-10), which can prevent the influx of neutrophils in the airway.

The targeting of proteins by the pIgR in humans provides an additional level of safety in vivo, since the fusion protein not delivered to the lung will be transported to the intestinal lumen, through either the enterocyte or in bile, where it will be excreted. Indeed, the trafficking pattern of the anti-human SC Fv-based fusion protein could also potentially be exploited to deliver relevant proteins to other tissues. The bile ducts and intestine are relatively inaccessible from the luminal surface and could also be targeted in this manner.

The expression and tissue distribution of the pIgR in rodents is different from that observed in humans (35,36). In rodents, the expression of the receptor is significantly greater in the liver than lung, based on the production of SC. Moreover, fifty per cent of the radiolabeled dIgA injected into the systemic circulation is rapidly transported from blood to bile by rat hepatocytes, while less than two per cent was detected in the lung after two hours (37). The clearance and tissue distribution of rabbit-derived, anti-SC Fab antibodies in rats are similar to the natural ligand. Yet, rodents may still serve as a model for the delivery of fusion proteins to epithelia.

SLPI has potential advantages over $A_1AT$ as the antiprotease component of the bifunctional protein. SLPI is a potent antagonist of serine proteases that accounts for the majority of elastase inhibitory capacity of endobronchial secretions, and it also does not require glycosylation for its function or stability in serum (11,12). An analogous fusion protein can be produced using SLP, replacing human $A_1AT$ with SLPI. The gene encoding a bifunctional protein containing anti-human SC Fv linked to SLPI can be constructed using the same techniques described above. The entire SLPI cDNA from human respiratory epithelial cells can be amplified using primers for the antiprotease gene. Like the previous constructs, specific sites of recognition for restriction endonucleases, including a unique Cla I site, can be incorporated in human SLPI oligonucleotide primers to permit cloning into an expression vector. The gene encoding the SLPI can be inserted "in frame" into the cloning vector, the plasmid pRc/CMV, downstream to anti-human secretory component single chain Fv from monoclonal antibodies. The sequence of the chimeric gene can be readily confirmed. Other proteins which may be used as therapeutic components of the fusion protein include cytokines, interleukin-2, interleukin-10, and peptide antibiotics.

The fusion protein may comprise other polyamino acid sequences, in addition to the single chain antibody and the therapeutic protein. Linker regions may be desirable to space the two portions of the protein from each other and to provide flexibility between them. Typically these will be less than 30 amino acid residues, and consist of predominantly neutral residues. Other moieties may also be included, as desired. These may include a binding region, such as avidin or an epitope, which may be useful for purification and processing of the fusion protein. In addition, detectable markers may be attached to the fusion protein, so that the traffic of the fusion protein through a body or cell may be monitored conveniently. Such markers may include radionuclides, enzymes, fluors, etc.

The fusion proteins of the invention are particularly useful for administration to epithelial cells. Thus airway epithelial cells and intestinal lumen cells are particularly good targets for the proteins. While any mode of administration to these organs will work, such as targeted or localized administration modes, the fusion proteins of the present invention can be administered systemically. The single chain antibody portion of the protein provide an excellent means of targeting, thus alleviating the need for targeted means of administration.

Suitable dosages for administration can be readily determined, and will depend somewhat on the therapeutic protein being delivered. However, typical dosage ranges will be between 0.05 mg and 500 mg, preferably between 0.5 mg and 50 mg, and more preferably between 1 mg and 10 mg. Due to the targeted nature of the fusion protein, lower dosages can be used of the therapeutic protein than are required when administering the therapeutic protein alone. In the case of the deliver of antiproteases to the cystic fibrosis lung, approximately 10–100 mg, preferably 70 mg, would need to be adminstered intravenously to achieve protection against neutrophil elastase.

The following examples provide specific modes of carrying out the invention. However, the invention is not limited or defined by the scope of these examples.

EXAMPLES

Example 1

Targeting the polymeric immunoglobulin receptor in vitro

We have shown that a complex consisting of the Fab portion of rabbit-derived, polyclonal antibody raised against human SC covalently linked to poly (L-lysine) will bind and condense plasmid DNA (Ferkol, et al. (1993) Gene transfer into respiratory epithelial cells by targeting the polymeric immunoglobulin receptor. *J Clin. Invest.* 93: 2394–2400.) The complexes effectively delivered foreign genes to human tracheal epithelial cells in culture which were induced to express pIgR (38). Delivery was specific for cells in culture that express the receptor, since human tracheal epithelial cells grown on plastic, a condition that down-regulates the expression of the receptor, fail to express the reporter gene whereas cells from the same trachea maintained on collagen gels can be transfected. Delivery of DNA is inhibited by excess human SC in the medium, which presumably occupies the recognition site on the Fab fragment, preventing its interaction with the receptor. However, competition for the pIgR with dIgA in a four-fold molar excess failed to block the delivery of the complex, perhaps indicating that the binding site(s) on the pIgR for dIgA and antibody do not overlap. Alternatively, the natural ligand may not compete effectively with the anti-human SC for the receptor, or the receptor may be present in excess. Uptake is not due to a non-specific increase in pinocytosis secondary to the presence of the Fab fragment in the culture medium, since the use of complexes with Fab fragments from irrelevant antibodies did not permit expression of reporter genes.

A variable percentage of human tracheal epithelial cells in primary culture were transfected through the pIgR. We have shown that differences in receptor expression in the cultured cells accounts for much of the observed variation. The proportion of human tracheal epithelial cells in culture which express pIgR which is detectable by immunofluorescence ranged from eight to thirty-five per cent, compared to five to sixty-six per cent of the cells which express the reporter gene delivered by the conjugate. The expression of the reporter gene co-localized to cells that expressed the receptor, as identified by immunohistochemical means. Thus, conjugates containing Fab fragments directed against human SC mediated the in vitro uptake of macromolecules into cells that expressed pIgR (38).

Example 2

Targeting the polymeric immunoglobulin receptor in vivo

Figure 2:
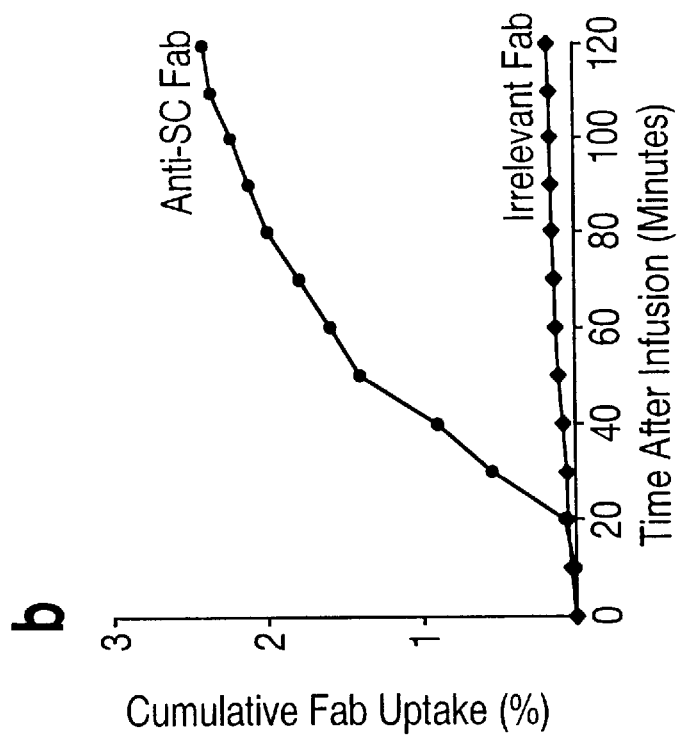
Figure 2:
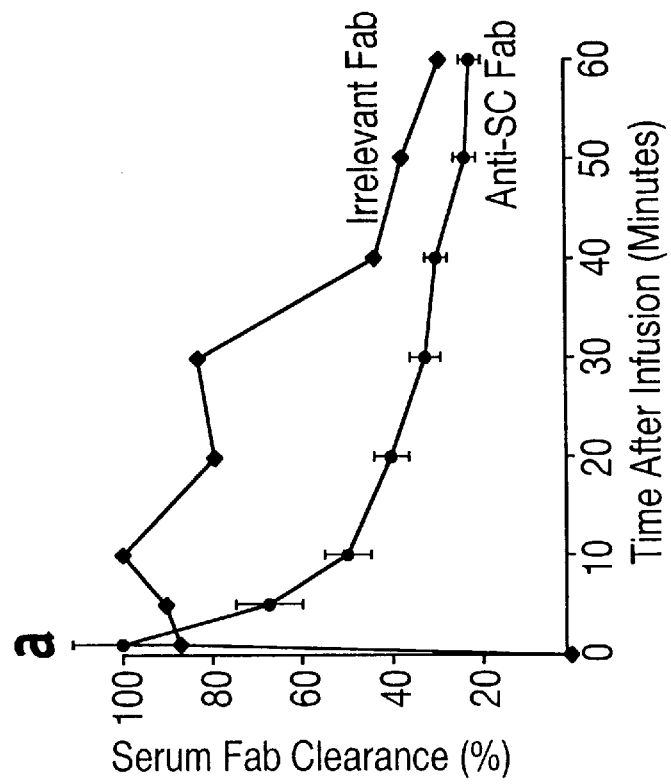

We have examined the pattern of transport of the anti-rat SC Fab fragments in adult rats to determine if these antibodies have the same vascular distribution and clearance as dIgA. Fifty micrograms of the anti-rat SC antibodies were injected into the systemic circulation, and serial samples of bile and blood were collected every ten minutes and examined for the rabbit-derived antibody by enzyme-linked immunosorbent assay (ELISA). The anti-SC Fab was rapidly cleared from the blood, and the antibody appeared in the bile twenty minutes after infusion (FIG. 2). No uptake in the bile was noted after injection with pre-immune rabbit-derived Fab antibody (FIG. 2). The rat anti-SC Fab, however, was not detected in BAL fluid obtained two hours after injection, which may be related to the fifty-fold dilution of ELF. In addition, BAL preferentially samples the alveolar space, where the receptor is not expressed.

Example 3

The pIgR was exploited for gene delivery into rats in vivo (Ferkol, et al., . (1995) Gene transfer into airways in animals by targeting the polymeric immunoglobulin receptor. *J Clin. Invest.* 95: 493–502.). Because the receptor is asymmetrically distributed, predominantly on the basolateral surface of epithelial cells, the complex should best be delivered by the systemic circulation. In our initial experiments, we tested the transfer of reporter genes into the lungs and livers of rats (39). Two tissues that do not express the pIgR, heart and spleen, were also tested as controls. Three hundred micrograms of the expression plasmid pGL2, consisting the SV40 viral promoter and enhancer ligated to the *Photinus pyralis* luciferase gene inserted into the *Escherichia coli* pUC19 vector, complexed to the anti-SC Fab-polylysine conjugate into the caudal vena cava of rats. Luciferase expression was found in the homogenates from the liver and lungs, but not spleen and heart. Animals treated with the complexes containing either an irrelevant plasmid or the bonafide expression plasmid bound to a carrier based on an irrelevant Fab fragment resulted in no significant luciferase activity in any tissue examined. Thus, only tissues that contain cells bearing pIgR are transfected, and transduction cannot be attributed to nonspecific uptake.

Specifically, transgene expression in the rats was greatest in the lung and less in liver, despite the recovery of the anti-rat SC Fab preferentially in bile. Thus, the airways are clearly accessed by the transfection complex in substantial amounts. Although, when we examined cellular distribution of the transgene, only seventeen per cent of the tracheal epithelial cells were positive for bacterial β-galactosidase. A more sensitive reporter (i.e., interleukin-2 receptor gene), however, showed that the majority of tracheal epithelial cells expressed the transgene. These data demonstrate the ability of transfection complexes directed only by the anti-SC Fab to access airway epithelial cells after intravenous administration (39).

Example 4

Figure 3:
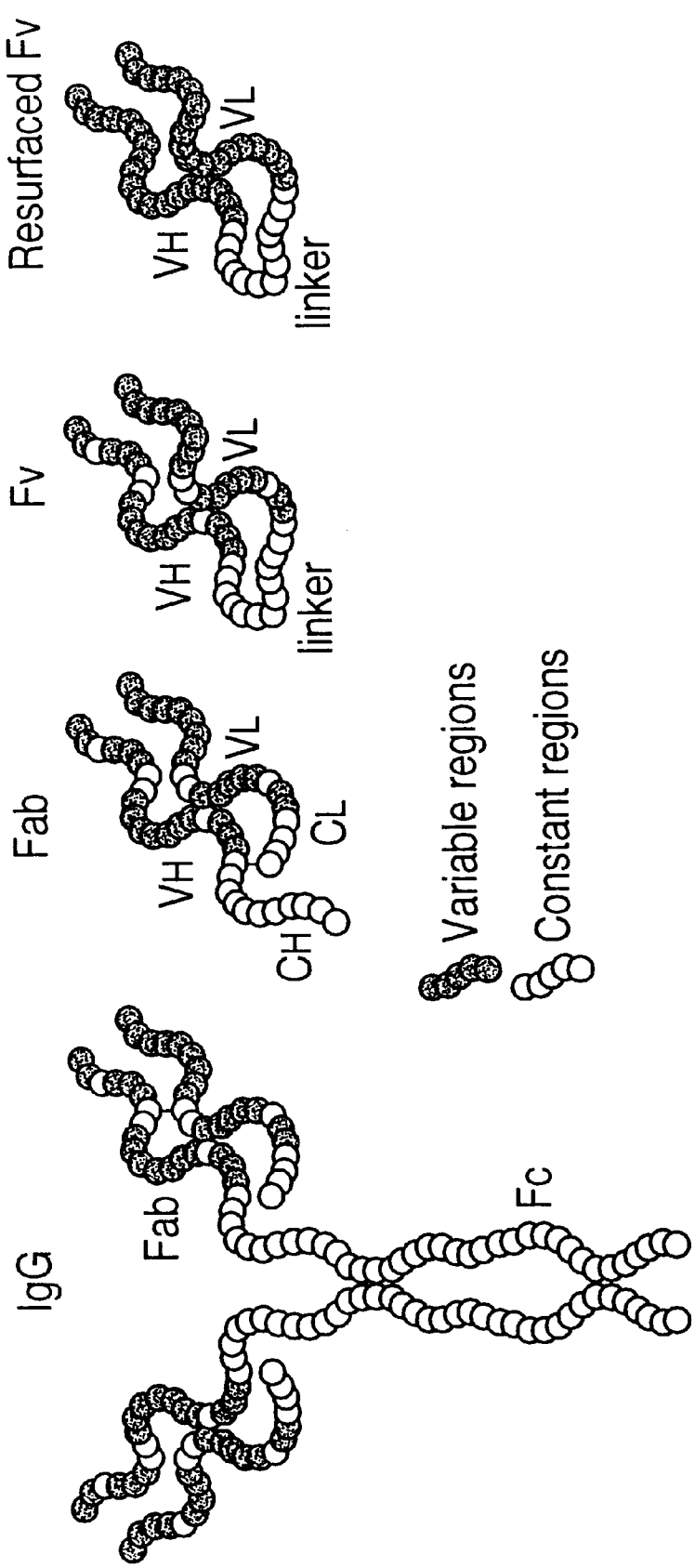

Because of this serologic response, the molecular conjugates were subsequently modified to reduce their immunogenicity. Specifically, anti-SC Fv fragments have been synthesized as ligands (FIG. 3). This approach requires the construction of monoclonal antibodies to replace the polyclonal antibodies used in the studies described above, and then prepare a single chain Fv. This strategy removes the species-specific constant regions of the Fab, leaving only the framework regions in the variable domain that are still murine-specific. Finally, since the peptide binding domain for the polymeric immunoglobulin receptor has not been mapped and probably is a three-dimensional region composed of sequences from both IgA molecules and connecting J chain (41), there are no peptide alternatives that could be used to target this receptor.

Example 5

Production of monoclonal antibodies against the human polymeric immunoglobulin receptor Balb/c mice were hyperimmunized with purified human SC, which was isolated from human colostrum. The mice underwent intraperitoneal injections with human SC, subcutaneous injection with Freund's adjuvant, and bled weekly. An ELISA was used to detect the production of antibodies directed against human SC. Three of the five inoculated mice showed a substantial response in serum against the antigen two weeks after the second immunization. Spleens were harvested from two mice and used in fusion experiments with the SP2/0 mouse myeloma cell line using a standard approach for the generation of hybridomas (42).

Figure 4:
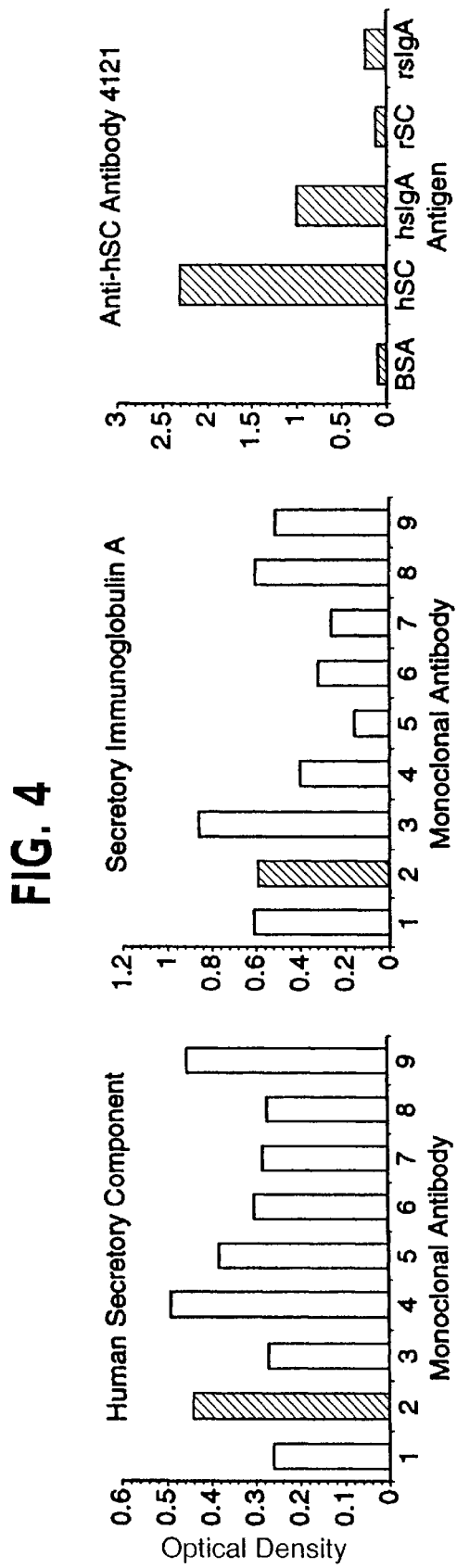

The hybridoma cells were then placed in selective media containing hypoxanthine and thymidine, which eliminates myeloma cells that have not fused, and their supernatants were analyzed for the production of anti-human SC antibodies. Positive hybridomas were cloned twice by limiting dilution, and several subclones continued to produce of anti-human SC antibodies, as detected by ELISA. Monoclonal antibodies against human SC were generated, all of which cross-react with purified human SC (FIG. 4) and sIgA (FIG. 4). Therefore these antibodies most likely recognize epitopes other than the binding site of the natural ligand. Based on analysis using a fluorescence activated cell sorter (FACS), the monoclonal antibodies 4121 and 4214 were selected for the initial experiments because they best recognized the receptor expressed on the surface of MDCK cells transduced with the cDNA encoding the human pIgR.

Example 6

Expression plasmids encoding Fv fragments of anti-human secretory component

The $V_L$ and $V_H$ portions of the anti-human SC antibodies were cloned from the hybridoma cell lines. Total cellular RNA was extracted from the antibody-producing cells, and the MrRNA transcripts were treated with Moloney Murine Leukemia Virus reverse transcriptase using random hexamers as primers. The resultant cDNA were screened for the $V_L$ and $V_H$ domains using different oligonucleotide primers, as described by Nicholls and colleagues (43), and these sequences were amplified by the polymerase chain reaction (PCR). The DNA sequences were spliced, separated by an interdomain linker that encodes fourteen or fifteen amino acids using a PCR technique called overlap extension (28, 43). Molecular modeling (44) and nuclear magnetic resonance analysis (45) have shown the optimal size of the linker in a single chain Fv has been determined to be greater than 12 amino acids. The use of glycine as the predominant amino acid in the linker permits the greatest molecular flexibility, thus allowing the two domains to fold properly and assume the proper orientation with each other. The cDNA encoding the $V_L$ and $V_H$ domains of the anti-human SC Fv were inserted into the expression vector downstream to the promoter for T3 RNA polymerase. The domains of the single chain Fv was assembled in the order $V_L$-linker-$V_H$, though either orientation has been used to produce functional Fv fragments. The anti-human SC Fv cDNA was sequenced by dideoxy chain termination.

Example 7

Chimeric genes encoding anti-secretory component Fv and human alpha$_1$-antitrypsin The cDNA sequences encoding the anti-human SC Fv from monoclonal antibody 4121 and irrelevant antibody directed against an anti-Pseudomonas polysaccharide (D8) was amplified through 30 cycles, using the following primers for the Fv: GG CCC AAG CTT GCC ACC ATG GAC ATT GTG CTG, a primer to detect the 5' region, and CCT AGT CTA GAC TTA CAT CGA TGA GGA GAC TGT GAG AGT GGT GCC, an antisense primer. The Kozak start sequence was placed immediately upstream of the Fv sequences to permit the optimal translation efficiency of the fusion protein in eukaryotes (46). Additional sequences encoding anti-human SC Fv isolated from other hybridoma clones are currently being generated which will serve as alternative ligands.

The entire human A$_1$AT cDNA was amplified, using primers for the human A$_1$AT gene: GAG CCA TCG ATG CCG TCT TCT GTC TCG TGG, a primer to the 5' end, and CCT AGT CTA GAT AAG CTT TTA TTT TTG GGT GGG ATT CAC, an antisense primer that corresponded to the 3' end of the gene. Specific sites of recognition for restriction endonucleases—Hind III, Cla I, and Xba I sites in the Fv cDNA and the human A$_1$AT primers were incorporated into both sets of primers to permit the excision of the intact chimeric gene and their cloning into the expression vector "in-frame."

Figure 5:
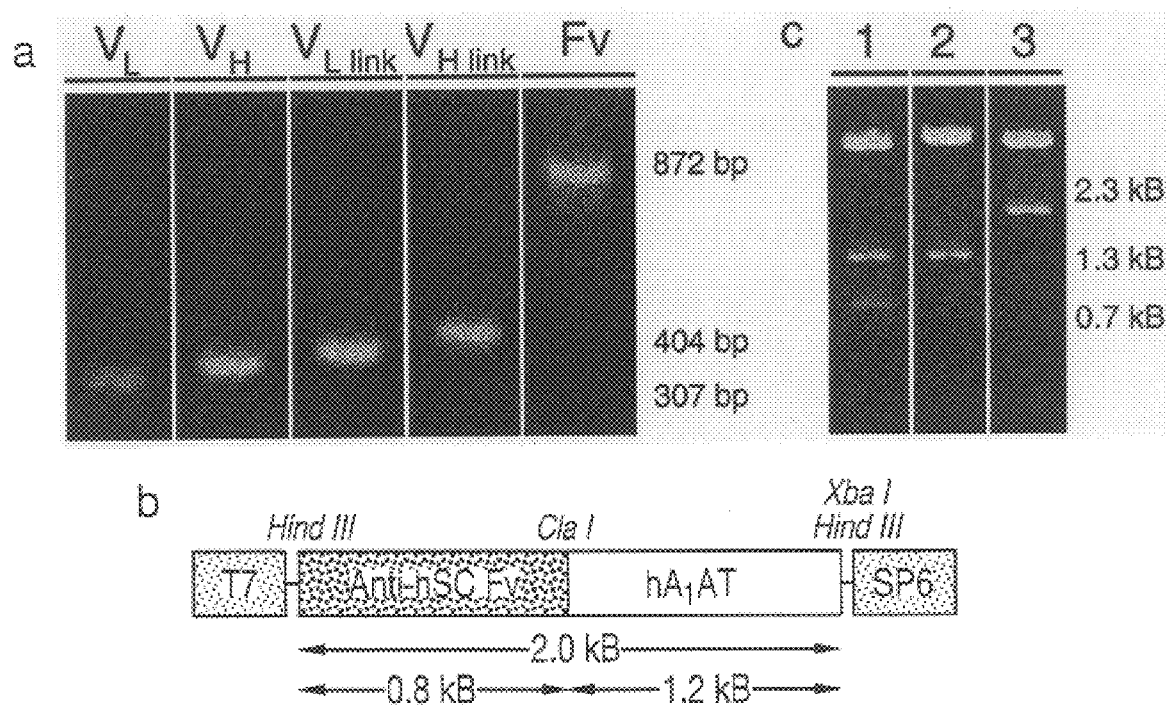

An *E. coli* cloning vector (pRc/CMV) was used to construct the anti-human SC Fv/human A$_1$AT chimeric gene. The vector pRc/CMV is designed for high level, stable expression in eukaryotic cells, and contains a multiple cloning site polylinker, cytomegalovirus promoter and enhancer, and bovine growth hormone polyadenylation signal. The vector also contains a neomycin resistance gene driven by the SV40 early promoter for the selection of stable transformants. This plasmid was digested with Hind III and Xba I, thus removing a segment of the multiple cloning site, and the amplified cDNA encoding the anti-human SC Fv will be inserted. This construct was digested with Cla I and Xba I, and the amplified cDNA encoding human A$_1$AT was ligated into this site in the same transcriptional orientation as the anti-SC Fv (FIG. 5). No episomal origin of replication is present in the plasmid. The nucleotide sequences of the 5' and 3' ends of the chimeric gene have been examined by dideoxy chain termination, and no rearrangements have been noted. Moreover, the fidelity of the chimeric gene was verified by restriction site analysis (FIG. 5).

Once the chimeric gene was constructed, it could be shuttled into appropriate prokaryotic or eukaryotic expression vectors via Hind III sites on both termini. For expression in prokaryotes, the anti-human SC Fv/human A$_1$AT chimeric gene was excised by digestion with Hind III, and ligated into the plasmid pQE-30 (Qiagen Inc., Chatsworth, Calif.). The gene is driven by the *E. coli* phage T5 and two lac operon sequences to eliminate expression prior to induction with isopropyl-β-D-thiogalactopyranoside (IPTG). This vector also contains a ribosome binding site and ampicillin resistance gene. A sequence encoding a polyhistadine (HHHHHH) label is located upstream in this vector that permits the identification and purification of the translated recombinant protein on a nickel-NTA resin column (47). Both prokaryotic and eukaryotic expression plasmids containing the cDNA encoding the anti-human SC and human A$_1$AT alone were constructed, and a fusion protein containing an irrelevant anti-D8 Fv fragment ligated to the human A$_1$AT was produced as control.

Figure 6:
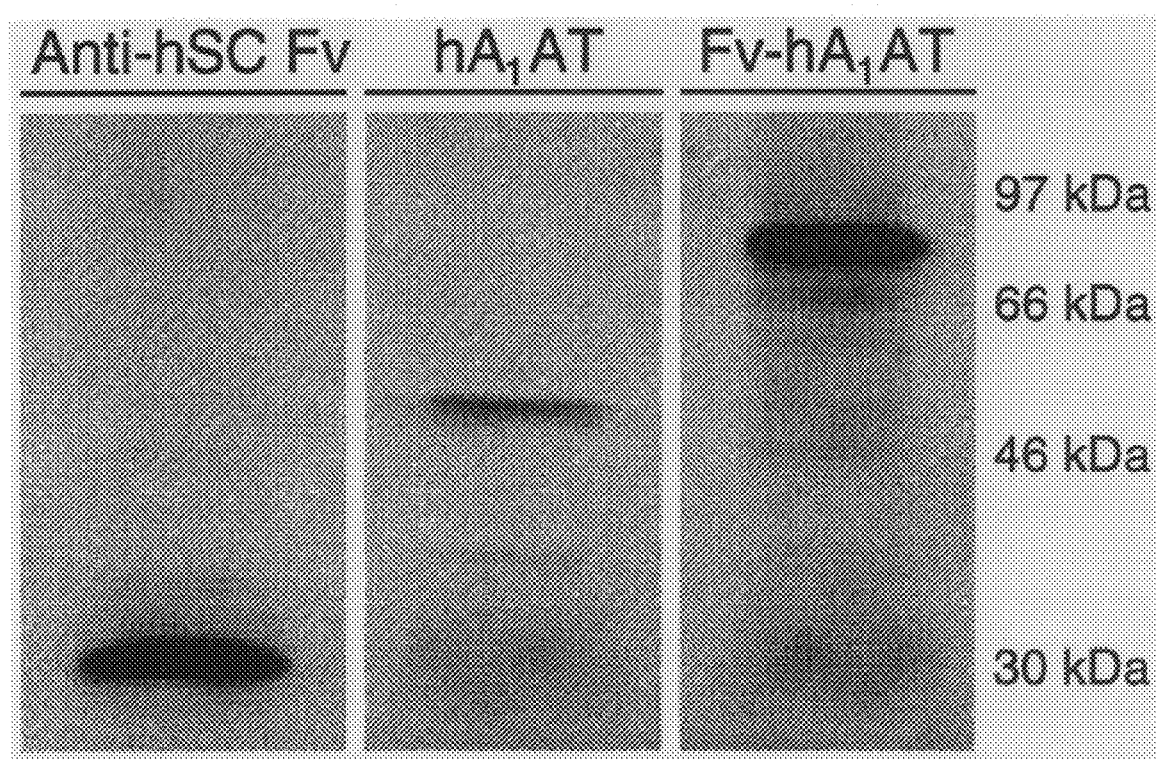

In vitro transcription and translation of the chimeric gene was performed using a rabbit reticulocyte lysate system to determine if the chimeric gene encoding anti-human SC Fv/human $A_1AT$ could be expressed. Messenger RNA encoding the chimeric genes was generated by transcribing the expression plasmid with T7 RNA polymerase, which was then translated in reticulate lysates using a coupled TNT system (Promega, Madison, Wis.). The synthesized proteins were radiolabeled by adding [$^{35}$S] methionine to the translation reaction. Analysis of the lysates by electrophoresis in SDS-polyacrylamide gels demonstrated the presence of the appropriately sized proteins for the anti-human SC Fv, human $A_1AT$, and fusion protein (FIG. 6).

Figure 7:
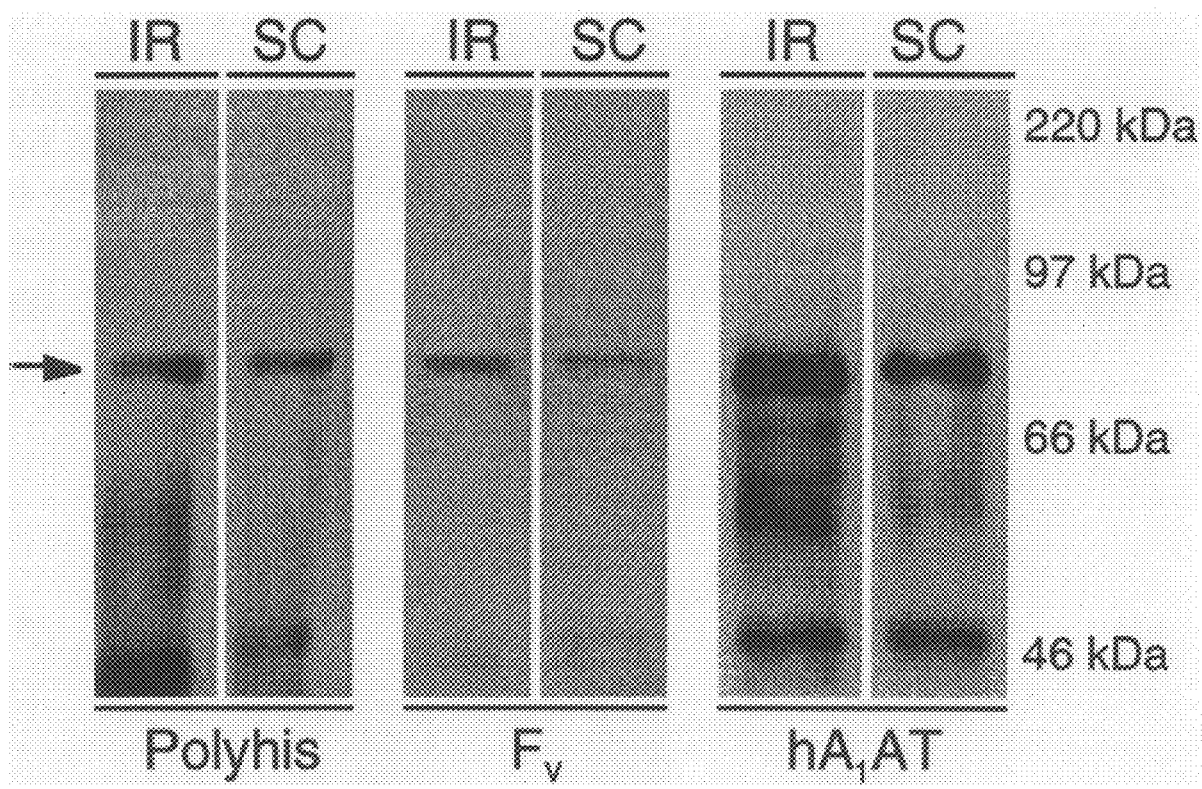

Example 8
Production of anti-human secretory component Fv/human alpha$_1$-antitrypsin fusion protein in prokaryotes Most single chain Fv constructs have been produced in bacteria because prokaryotes can produce large quantities of the fusion protein. E. coli strain M15[pREP4] was transduced with a plasmid containing the anti-human SC Fv/human $A_1AT$ chimeric gene driven by the E. coli phage T5, and ampicillin resistant clones were selected in LB media containing 100 mg/mil ampicillin. Protein extracted from isolated inclusion bodies of transformed bacterial clones were purified by nickel-chelate affinity chromatography, exploiting the polyhistadine tag, subjected to electrophoresis in SDS-polyacrylamide gels, and transferred onto nitrocellulose membrane filters using established methods. The protein products were identified by Western blot analysis using antibodies directed against the individual components, i.e., polyhistadine tag, single chain Fv fragments, and human $A_1AT$, which demonstrated the same intact, non-glycosylated fusion protein (FIG. 7). In order to recover function since protein from cytoplasmic inclusion bodies are inactive, the Fv-based fusion proteins was to be solubilized and renatured by diluting resultant fusion proteins (48). We have tried several refolding techniques, and dilution appears to be the most effective approach of renaturing the fusion protein produced in prokaryotes, although the efficiency of the process is uncertain.

Large-scale production of the fusion proteins will be critical for experiments examining the transport through the pIgR in vitro and in vivo. Although prokaryotes can produce large quantities of recombinant proteins, Fv-based fusions produced by bacteria needs to be solubilized and renatured in order to recover function since proteins purified from cytoplasmic inclusion bodies are inactive due to the harsh conditions necessary to solubilize them (48). Human $A_1AT$ has been successfully made by E. coli and it retains protease inhibition (49), but non-glycosylated forms of the antiprotease has an extremely short half-life in the circulation, decreasing the antiprotease half-life to hours (50). The shortened lifespan of the recombinant human $A_1AT$ may not matter so much for our fusion proteins, since seventy-five percent of the anti-SC antibody is cleared from the circulation in one hour. Thus, we are confident that the single chain anti-human SC Fv/human $A_1AT$ fusion produced by prokaryotes will be adequate for experiments in vitro, but may have limited usefulness in vivo.

Figure 8:
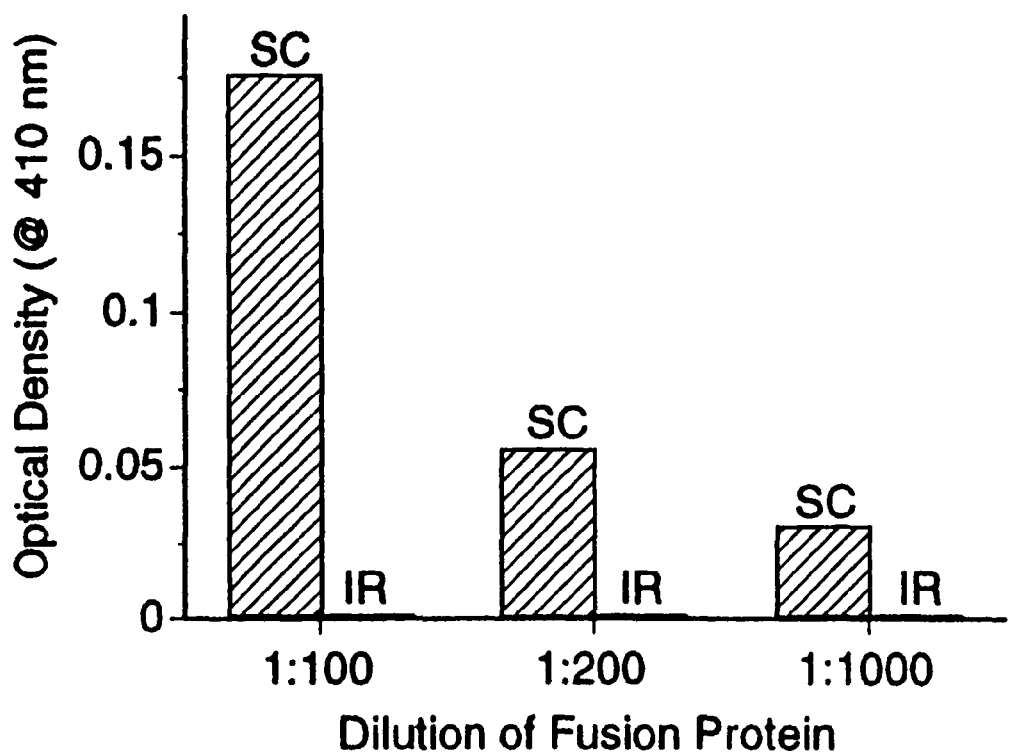

Example 9
Recognition of the human secretory component by anti-human secretory component Fv ELISA was used to demonstrate that the single chain Fv portion of the fusion protein recognizes human SC. Human SC was incubated in each well of a 96 well microtiter plate, washed, and blocked. The fusion proteins synthesized by bacteria were isolated and refolded using standard techniques, then added to the wells. After washes, a rabbit-derived, polyclonal anti-human $A_1AT$ and goat-derived, anti-rabbit (Fab')$_2$ conjugated with horseradish peroxidase were applied sequentially and used to detect the antiprotease portion of the protein. The fusion proteins containing the anti-human SC Fv effectively bound to the sIgA, whereas fusions containing an irrelevant (anti-D8) Fv did not (FIG. 8). Because the Fv portion of the molecule recognizes human SC, the fusion protein used in later experiments could be purified by affinity column chromatography.

Thus, transformed bacteria can yield fusion proteins that recognize human SC, so the single chain Fv component is functional. This protein is also recognized by antibodies directed against both parts of the bifunctional protein. Specifically, a commercially-available anti-human $A_1AT$ antibody and an antibody we prepared against the framework regions covered by the oligonucleotide primers and used to generate the single chain Fv fragments. The polyhistidine tag from the expression vector was recognized by the appropriate antibody, so all three immunologically recognizable components of the fusion are present.

Example 10
Production of anti-human secretory component Fv/human alpha$_1$-antitrypsin fusion protein in eukaryotic cells On a theoretical basis, prokaryotes may not be the best expression system, since they fail to process and glycosylate mammalian proteins appropriately. For $A_1AT$, glycosylation stabilizes the protein in blood though the antiprotease activity is unaffected. It is likely that stabilization will be more important for the native $A_1AT$ than for fusion proteins, which our data suggest will be rapidly directed to the site of action by the single chain Fv, it could be important and may represent an antigenic difference that is not desirable. Thus, it would be preferable to replicate the native $A_1AT$, and the antiprotease component of the fusions may need to undergo post-translational processing by eukaryotic cells for this strategy to be successful.

Eukaryotic cells can effectively secrete single chain Fv proteins, which may be necessary for the large-scale production and purification of the fusion protein. The chimeric gene was altered to introduce an immunoglobulin light chain leader sequence to the 5' terminus of the Fv which will permit the secretion of the fusion protein by eukaryotic cells (51). The cDNA encoding the anti-human SC Fv from monoclonal antibody 4121 was amplified through 30 cycles, using the following primers for the immunoglobulin light chain leader sequence and Fv: GCG CCC AAG CTT GCC ACC ATG AGG ACC CCT GCT CAG TTT CTT GGA ATC TTG TTG CTC TGG TTT CCA GGT ATC AAA TGT GAC ATT GTG CTG ACC CAG TCT CC, a primer to detect the leader sequence and 5' region of the single chain Fv and CCT AGT CTA GAC TTA CAT CGA TGA GGA GAC TGT GAG AGT GGT GCC, an antisense primer. The Kozak start sequence was again inserted upstream to the leader sequence. Specific recognition sites for the restriction endonucleases Hind III, Xba I, and Cla I were included in the primers to permit ligation into a cloning vector. The vector pRc/CMV was used to assemble the chimeric gene encoding anti-human SC Fv/human $A_1AT$. This plasmid was digested with Hind III and Xba I, and the amplified cDNA encoding the anti-human SC Fv was inserted; this intermediate was digested with Cla I and Xba I, and cDNA encoding human $A_1AT$ ligated into the site in the same transcriptional orientation.

Insect cells have received considerable attention as prolific factories for proteins. We have since examined the synthesis of fusions by transfected *Drosophila melanogaster* (S2) cells. The chimeric gene encoding anti-human SC Fv/human $A_1AT$ was ligated into the multiple cloning site of the pUC-hygMT expression plasmid at BamHI and XhoI sites in the same transcriptional orientation as the mouse metallothinein 1 promoter regulatory region (52). This vector also contains hygromycin and ampicillin resistance genes to permit selection. Using Lipofectin, S2 cells were transduced in suspension with the plasmid, and two days after transfection, expression of the transgene was induced by treating the cells with 0.5 mM copper sulfate for 24 hours (52). Cell lysates were collected and the proteins were separated by 10% SDS-polyacrylamide gel electrophoresis. The full length fusion protein was detected by Western blot hybridization using an anti-human $A_1AT$ antibody in cell lysates at concentrations of approximately 100 ng/ml. In preliminary studies, transfected S2 cells after selection secreted 3 to 5 μg/ml of the fusion protein into the media, as measured by ELISA that recognizes human SC. We are currently producing high-expression clones. If fusions synthesized by the transduced cells can continue to be produced in sufficient quantity and proves to be bifunctional, we will perform many of the proposed experiments with these products.

Example 11
Transcytosis of the anti-secretory component antibodies and Fv fragments Human tracheal epithelial cells grown in primary culture on collagen gels maintain production of pIgR. However, expression of the receptor differs among preparations. Cells stained in situ for human SC indicated that the expression of the production of pIgR in primary tracheal epithelial cells is variable, ranging from eight to thirty-five per cent of cells in culture, with a mean of twenty-two per cent by fluorescent activated cell sorter analysis. Because of this variability, the tracheal epithelial cells are not a suitable model for our investigations.

Figure 9:
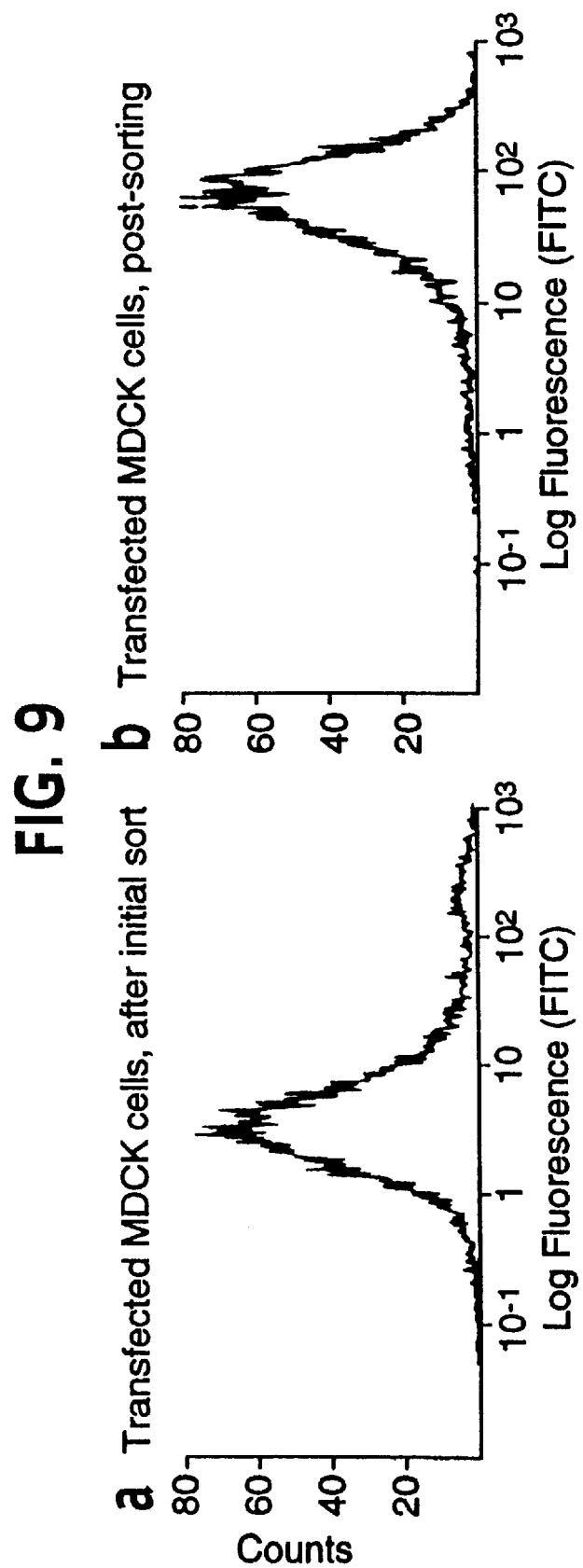
Figure 10:
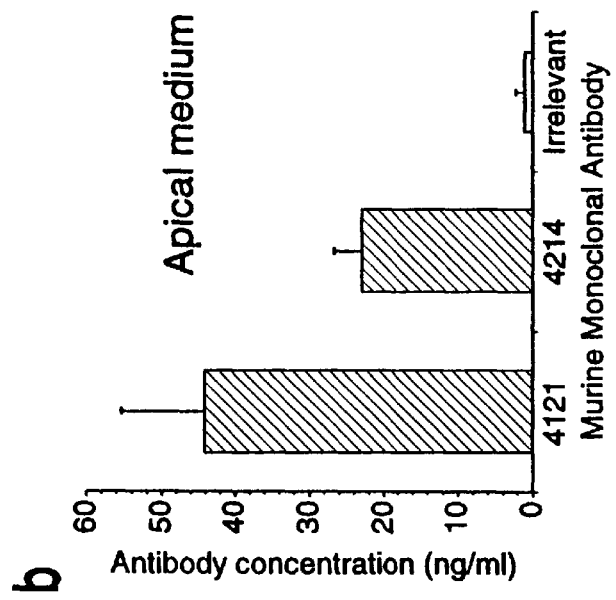
Figure 10:
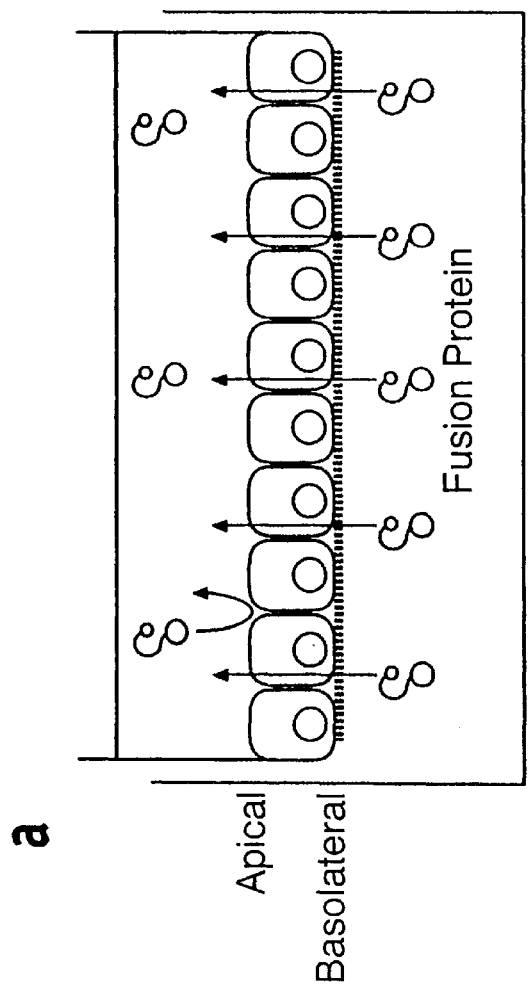

Madin-Darby canine kidney (MDCK) cells transfected with rabbit pIgR cDNA have been used extensively by several investigators as a method of examining the trafficking of the receptor (53,54). We have developed a similar system for the transport of the human receptor in polarized cells. MDCK cells were transduced with the gene encoding the human pIgR. Stably transfected cells were selected for neomycin resistance, and positive cells were sorted repeatedly for the highest level of the human pIgR by a fluorescent activated cell sorter (FIG. 9). More recently, we have selected individual, high expression cells and expanded the clones. When grown on porous filters, the transduced MDCK cells appropriately traffic the human pIgR and the natural ligand dIgA from the basolateral to the apical membrane. The transport of the anti-human SC monoclonal antibodies across the cells expressing the human pIgR was also examined. Fifty micrograms of the monoclonal antibodies 4121 and 4214 applied to the basolateral surface of a monolayer of these cells. The anti-human SC monoclonal antibodies were transported to the apical surface, where they were released into the media (FIG. 10). Irrelevant monoclonal antibodies applied to the basolateral surface were not transported. None of the antibodies were trafficked across the cells in the opposite (i.e., apical-to-basolateral) direction. Thus, we have the ability to examine the transcytosis of proteins via the human pIgR, and we will use the cellular models to assess the efficiency of cellular transport of the bifunctional proteins.

Figure 11:
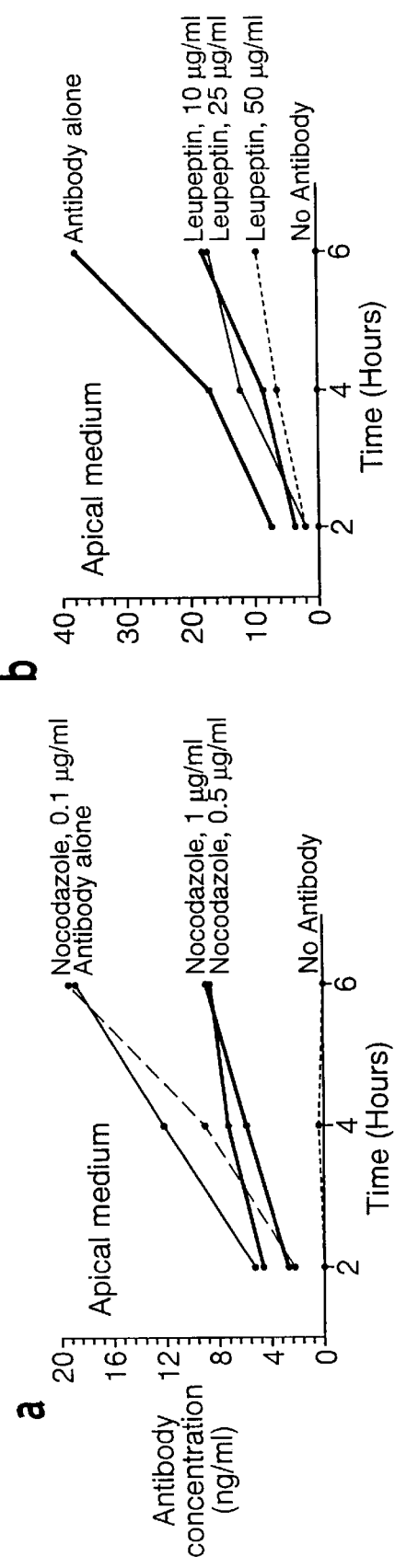

Epithelial cells have distinct apical and basolateral surfaces, and maintain their polarity with cytoskeletal elements. Microtubules are critical for fusion of endosomal vesicles, transcytosis of several proteins, and apical recycling. Colchicine and nocodazole (55,56), agents that disrupt microtubule function, are reported to disrupt pIgR transcytosis while sparing endocytosis process. We examined the effects of nocodazole on the trafficking of monoclonal anti-human SC antibody across transduced MDCK cells that express the receptor. Fifteen micrograms of the intact monoclonal antibody was added to the basolateral media, and apical media was collected at different times. Nocodazole (concentration range, 0.1–1 μg/ml) markedly reduced the transcytosis of anti-human SC antibody (FIG. 11).

Once the pIgR and antibody reach the apical surface of the cell, the extracellular portion of the receptor is cleaved and the ligand, still bound to SC, is released at the apical surface. If cleavage does not occur, SC will not be released. We tested the ability of leupeptin, which inhibits the cleavage of pIgR, to block the release of the monoclonal antibody (57). Indeed, increasing concentrations of leupeptin (concentration range, 10–100 μg/mil) reduced the amount of antibody detected in the apical medium (FIG. 11).

We subsequently examined the transcytosis of the intact anti-human SC antibody (4121) chemically conjugated to human $A_1AT$ across a monolayer of transduced MDCK cells that appropriately traffic the human pIgR. When grown on a collagen support, these cells are polarized and transport the pIgR from the basolateral to the apical membrane, where SC is released. Molecular conjugates containing anti-rat SC immunoglobulin G was bound to human $A_1AT$ by the heterobifunctional cross-linking reagent N-Succinimidyl 3-(2-pyridyldithio) proprionate (SPDP) using established techniques (38,39). The resultant conjugate (1 μg $A_1AT$ content) was added to the basolateral media of a monolayer of these cells, media from the apical surface was collected at different times and examined for the presence of the human $A_1AT$ by ELISA. Conjugates containing irrelevant monoclonal antibodies (anti-D8) were examined in parallel as a control. Consistently, anti-human SC/human $A_1AT$ conjugate was transported in the basolateral-to-apical direction across the MDCK cells that express human pIgR (FIG. 12). The conjugate containing an irrelevant Fv was not transported across the monolayer. Virtually no transport of the fusion proteins occurred in the opposite, apical-to-basolateral direction.

We have examined the transport of affinity purified fusion proteins containing the anti-human SC Fv (2 μg $A_1AT$ content), produced by stably transfected *D. melanogaster* S2 cells, across cell monolayers. The fusions were effectively transported in the basolateral-to-apical direction across the receptor-expressing MDCK cells (FIG. 13). Substantially less fusion protein was transported across these cells in the opposite direction (FIG. 13). No purified human $A_1AT$ was transported across the monolayer in either direction. Neither the fusion protein or human $A_1AT$ was transported across a monolayer of non-transduced MDCK cells. In addition, fusion protein that was transported across the transduced MDCK cells to the apical compartment was bound to SC (refer to FIG. 1). The fusion proteins transported to the apical media were isolated by immunoprecipitation with a monoclonal antibody specific for human secretory component. The bound proteins were then subjected to electrophoresis in SDS-polyacrylamide gels, transferred onto a nitrocellulose membrane filter, and the human $A_1AT$ component of the fusion was detected by Western blot hybridization. Neither the non-transported fusion nor purified human $A_1AT$ were recognized by the anti-human SC antibody and precipitated. So, the uptake of the fusion was mediated by the specific interaction of the anti-SC antibody with the human pIgR, and these constructs were transported to the apical surface of cells in vitro.

Example 12

Antiprotease activity of the anti-human secretory component Fv/human alpha$_1$-antitrypsin fusion protein The other component of the fusion protein, human A$_1$AT, was functional, based on the ability of the fusion to complex elastase. Inhibition of NE is the major physiological function of A$_1$AT, which neutralizes free elastase by permitting the enzyme to bind directly to a substrate-like region within the carboxy-terminus region of the antiprotease, resulting in a complex that contains one molecule of each of the reactants. The fusion protein (100 ng A$_1$AT content) was incubated with an equimolar amount of purified NE for 30 minutes at room temperature, and the resultant products were separated by SDS-polyacrylamide gel electrophoresis. Western blot hybridization of the products using a rabbit-derived, polyclonal anti-human A$_1$AT showed a distinct size shift of the fusion protein FIG. 14). The human A$_1$AT was partially degraded if excess antiprotease was added to the reaction. Moreover, human SC bound to the fusion did not appear to effect the binding of the antiprotease to elastase (FIG. 14). Thus, both components of the anti-human SC Fv/human A$_1$AT bifunctional protein are indeed functional.

Summary

We have developed a delivery system that exploits the pIgR and can target fusion proteins to the luminal surface of respiratory epithelium in patients. We have demonstrated, using transfection complexes, that the pIgR is successfully accessed by anti-SC Fab antibodies injected into the systemic circulation, and the majority of airway epithelial cells expressing the receptor can be targeted. Chimeric genes that encodes a fusion protein for single chain anti-SC Fv fragments linked to human A$_1$AT, that can be expressed in both prokaryotic and eukaryotic cells. We have produced a cell model that expresses and traffics the receptor appropriately. Both protein conjugates and fusions can be transported by this system in a vectorial fashion, and the antiprotease portion of the fusion protein is functional, based on the ability of the fusion to bind elastase.

LITERATURE CITED

1 Konstan, M. W., Byard, P. J., Hoppel, C. L., and Davis, P. B. 1995. Effect of high dose ibuprofen in patients with cystic fibrosis. N. Eng. J. Med. 332: 848–854.

2 Konstan, M. W., Hilliard, K. A., Norvell, T. M., and Berger, M. 1994. Bronchoalveolar lavage findings in cystic fibrosis patients with stable, clinically mild lung disease suggest ongoing infection and inflammation. Am. J. Respir. Crit. Care Med. 150: 448–454.

3 Richman-Eisenstat, J. B. Y., Jorens, P. G., Hebert, C. A., Ueki, I., and Nadel, J. A. 1993. Interleukin-8: an important chemoattractant in sputum of patients with chronic inflammatory airway disease. Am. J. Physiol. Lung Cell Mol. Physiol. 264: L413–418.

4 Lawrence, R. H. and Sorrelli, T. C. 1992. Decreased polymorphonuclear leucocyte chemotactic response to leukotriene B$_4$ in cystic fibrosis. Clin. Exp. Immunol. 89: 321–324.

5 Nakamura, H., Yoshimura, K., McElvaney, N. G., and Crystal, R. G. 1992. Neutrophil elastase in respiratory epithelial lining fluid of individuals with cystic fibrosis induces interleukin-8 gene expression in a human bronchial epithelial cell line. J.Clin.Invest. 89: 1478–1484.

6 Konstan, M. W. and Berger, M. 1993. Infection and inflammation of the lung in cystic fibrosis. In Davis, P. B. (ed.) Cystic Fibrosis. Marcel Decker, Inc. New York, N.Y. pp. 219–276.

7 Sommerhoff, C. P., Nadel, J. A., Basbaum, C. B., and Caughey, G. H. 1990. Neutrophil elastase and cathepsin G stimulate secretion from cultured bovine airway gland serous cells. J. Clin. Invest. 85: 682–689.

8 Goldman, M. J., Anderson, G. M., Stolzenberg, E. D., Kari, U. P., Zazloff M., and Wilson, J. M. 1997. Human β-defensin-1 is a salt-sensitive antibiotic in lung that is inactivated in cystic fibrosis. Cell. 88: 553–560.

9 McCray, P. B., and Bentley, L. 1997. Human airway epithelia express a β-defensin. Am. J. Resp. Cell. Mol. Biol. 16: 343–349.

10 Rice, W. G. and Weiss, S. J. 1990. Regulation of proteolysis at the neutrophil-substrate interface by secretory leukoprotease inhibitor. Science. 249: 178–181.

11 Abe, T., Kobayashi, N., Yoshimura, K., Trapnell, B. C., Kim, H., Hubbard, R. C., Brewer, M. T., Thompson, R. C., and Crystal, R. G. 1991. Expression of the secretory leukoprotease inhibitor gene in epithelial cells. J Clin Invest. 87: 2207–2215.

12 Tegner, H. 1978. Quantitation of human granulocyte protease inhibition in non-purulent bronchoalveolar lavage fluid. Acta Otolaryngol. 85: 282–289.

13 Jin, F. Y., Nathan, C., Radzioch, D., and Ding, A. Secretory leukocyte protease inhibitor: a macrophage product induced by and antagonistic to bacterial lipopolysaccharide. Cell. 88: 417–426.

14 DiMango, E., Zar, H. J., Bryan, R., and Prince, A. 1995. Diverse Pseudomonas aeruginosa gene products stimulate respiratory epithelial cells to produce interleukin-8. J. Clin. Invest. 96: 2204–2210.

15 Morse J. O. 1978. Alpha$_1$-antitrypsin (two parts) N Engl J Med. 299: 1045–1048, 1099–1105.

16 Gadek, J. E., Fells, G. A., Zimmerman, R. L., Rennard, S. I., and Crystal, R. G. 1981. Antielastases of the human alveolar structures: implications for the protease-antiprotease theory of emphysema. J. Clin. Invest. 68: 889–898.

17 O'Connor, C. M., Gaffney, K., Keane, J., Southey, A., Byrne, N., O'Mahoney, S., and Fitzgerald, M. X. 1993. α$_1$-Proteinase inhibitor, elastase activity, and lung disease severity in cystic fibrosis. Am. Rev. Respir. Dis. 148: 1665–1670.

18 Wewers M. D., Casolaro M. A., Sellers S. E., Swayse, S. C., McPhaul, K. M., Wittes, J. T., and Crystal, R. G. 1987. Replacement therapy for alpha$_1$-antitrypsin deficiency associated with emphysema. N. Engl. J. Med. 316: 1055–1062.

19 Hubbard R. C. and Crystal R. G. 1988. Alpha$_1$-antitrypsin augmentation therapy for alpha$_1$-antitrypsin deficiency. Am J Med. 84 (suppl 6A): 52–62.

20 McElvaney, N. G., Hubbard, R. C., Birrer, P., Chernick, M. S., Caplan, D. B., Frank, M. M., and Crystal, R. G. 1991. Aerosol α$_1$-antitrypsin treatment of cystic fibrosis. Lancet. 337: 392–394.

21 Brandzaeg, P. 1985. Role of J chain and secretory component in receptor-mediated glandular and hepatic transport of immunoglobulins in man. Scand. J. Immunol. 22: 111–146.

22 Breitfeld, P. P, Harris, J. M., and Mostov, K. E. 1989. Postendocytotic sorting of the ligand for the polymeric immunoglobulin receptor in Madin-Darby canine kidney cells. *J. Cell. Biol.* 109: 475–486.

23 Fiedler, M. A., Kaetzel, C. S., and Davis, P. B. 1991. Sustained production of secretory component by primary tracheal epithelial cells in primary culture. *Am. J. Physiol.* 261 (Lung Cell. Mol. Physiol.): L255–261.

24 Takamuri, T. and Eishi, Y. 1984. Distribution of SC and immunoglobulins in the developing lung. *Am. Rev. Respir. Dis.* 1318: 125–130.

25 Watts, C. L., Fanaroff, A. A., and Bruce, M. C. 1992. Fibronectin levels in lung secretions in respiratory distress syndrome. *J. Pediatr.* 20: 614–620.

26 Bird, R. E., Hardman, K. D., Jacobson, J. W., Johnson, S., Kaufman, B. M., Lee, S. M., Lee, T., Pope, S. H., Riordan, G. S., and Whitlow, M. 1988. Single-chain antigen-binding proteins. *Science.* 242: 423–426.

27 Huston, J. S., Levinson, D., Mudgett-Hunter, M., Tai, M. S., Novotny, J., Margolis, M. N., Ridge, R. J., Bruccoleri, R. B., Haber, E., Crea, R., Opperman, H. 1988. Protein engineering of antibody binding sites: recovery of specific activity in an anti-digoxin single chain Fv analogue produced in *Escherichia coli. Proc. Natl. Acad. Sci.* 85: 5879–5883.

28 Pantoliano, M. W., Bird, R. E., Johnson, S., Asel, E. D., Dodd, S. W., Wood, J. F., and Hardman, K. D. 1991. Conformational stability, folding, and ligand-binding affinity of single-chain Fv immunoglobulin fragments expressed in *Escherichia coli. Biochemistry.* 30: 10117–10125.

29 Colama, M. J., Hastings, A., Wims, L., and Morrison, S. 1992. Novel vectors for the expression of antibody molecules using variable regions generated by polymerase chain reactions. *J. Immunol. Meth.* 152: 89–104.

30 Batra, J. K., Fitzgerald, D. J., Chaudhary, V. K., and Pastan, I. 1991. Single-chain immunotoxins directed at the human transferrin receptor containing *Pseudomonas exotoxin* A or diphtheria toxin: anti-TFR(Fv)-PE40 and DT388-Anti-TFR(Fv). *Mol. Cell. Biol.* 11: 2200–2205.

31 Chaudhary, V. K., Queen, C., Junghans, R. P., Waldmann, T. A., FitzGerald, D. J., and Pastan, I. 1989. A recombinant immunotoxin consisting of two antibody variable domains fused to *Pseudomonas exotoxin. Nature.* 339: 394–397.

32 Smith, J. J., Travis, S. M., Greenberg, E. P., and Welsh, M. J. 1996. Cystic fibrosis airway epithelia fail to kill bacteria because of abnormal airway surface fluid. *Cell.* 85: 229–236.

33 Ramsey, B. W. 1996. Drug therapy: management of pulmonary disease in patients with cystic fibrosis. *N. Eng. J. Med.* 335: 179–188.

34 Bonfield, T. L., Konstan, M. W., Burfeind, P., Panuska, J. R., Hilliard, J. B., and Berger, M. 1995. Normal bronchial epithelial cells constitutively produce the anti-inflammatory cytokine interleukin-10, which is downregulated in cystic fibrosis. *Am.J.Respir.Cell.Mol. .Biol.* 13: 257–261.

35 Sullivan, D. A. and C. R. Wira. 1983. Variations in free secretory component levels in mucosal secretions of the rat. *J. Immunol.* 130: 1330–1335.

36 Huling, S., G. R. Fournier, A. Feren, A. Chuntharapai, and A. L. Jones. 1992. Ontogeny of the secretory immune system: Maturation of a functional polymeric immunoglobulin receptor regulated by gene expression. *Proc. Natl. Acad Sci. USA.* 89: 4260–4264.

37 Chintalacharuvu, K. R., A. S. Tavill, L. N. Louis, J. P. Vaerman, M. E. Lamm, and C. S. Kaetzel. 1994. Disulfide bond formation between dimeric immunoglobulin A and the polymeric immunoglobulin receptor during hepatic transcytosis. *Hepatology.* 19: 162–173.

38 Ferkol, T., Kaetzel, C. S., and Davis, P. B. 1993. Gene transfer into respiratory epithelial cells by targeting the polymeric immunoglobulin receptor. *J. Clin. Invest.* 93: 2394–2400.

39 Ferkol, T., Perales, J. C., Kaetzel, C. S., Eckman, E., Hanson, R. W., and Davis, P. B. 1995. Gene transfer into airways in animals by targeting the polymeric immunoglobulin receptor. *J. Clin. Invest.* 95: 493–502.

40 Ferkol, T., Pellicena-Palle, A., Eckman, E., Perales, J. C., Redman, R., Tosi, M., and Davis, P. B. 1996. Immunologic responses of gene transfer into mice via the polymeric immunoglobulin receptor. *Gene Ther.* 3: 669–678.

41 Brandtzaeg, P., Krajci, P., Kvale, D., and Sollid, L. M. 1989. Secretory component as a polymeric-Ig receptor: structural and functional aspects. In Kotyk, A., Skoda, J., Paces, V., and Kosta, V. (eds.) Highlights Modern Biochem. Zeist, VSP International Science Publishers. Vol 2, pp 1255–1266.

42 Oi, V. T. and Herzenberg, L. A. 1980. Immunoglobulin-producing hybrid cell lines. In Mishell, B. B. and Shiigi, S. M. (eds.). Selected Methods in Cellular Immunology. W. H. Freeman, pp. 351–372.

43 Nicholls, P. J., Johnson, V. G., Blanford, M. D., and Andrew, S. M. 1993. An improved method of generating single-chain antibodies from hybridomas. *J. Immunol. Methods.* 165: 81–91.

44 Johnson, S. and Bird, R. E. 1991. Construction of single-chain Fv derivatives of monoclonal antibodies and their production in *Escherichia coli. Methods Enzymol.* 203: 88–97.

45 Freund, C., Ross, A., Guth, B., Pluckthun, A., and Holak, T. A. 1993. Characterization of the linker peptide of a single-chain Fv fragment of an antibody by NMR spectroscopy. *FEBS Letters.* 320: 97–100.

46 Kozak, M. 1994. Determinants of translational fidelity and efficiency in vertebrate nRNAs *Biochemie.* 76: 815–821.

47 Hochuli, E., Bannwarth, W., Dobeli, H., Gentz, R., and Stuber, D. 1988. Genetic approach to facilitate purification of recombinant proteins with a novel metal chelate absorbent. *BioTechnology.* 6: 1321–1325.

48 Huston, J. S., Mudgett-Hunter, M., Tai, M. S., McCartney, J., Warren, F., Haber, E., and Opperman, H. 1991. Protein engineering of single-chain Fv analogs and fusion proteins. *Methods Enzymol.* 203: 46–78.

49 Courtney, M., Buchwalder, A., Tessier, L. H., Jaye, M., Benavente, A., Balland, A., Kohli, V., Lathe, R., Tolstoshev, P., and Lecocq, J. P. 1984. Highlevel production of biologically active human $\alpha_1$-antitrypsin in *Escherichia coli. Proc. Nat. Acad. Sci., USA.* 81: 669–673.

50 Travis, J., Owen, M. C., George, P., Carrell, R. W., Rosenberg, S., Hallewell, R. A., and Barr, P. J. 1985. Isolation and properties of recombinant DNA produced variants of human alpha$_1$-proteinase inhibitor. *J. Biol. Chem.* 260: 4384–4393.

51 Jost, C. R., Kurucz, I., Jacobus, C. M., Titus, J. A., George, A. J. T., and Segal, D. M. 1994. Mammalian 51. expression and secretion of functional single-chain Fv molecules. *J. Biol. Chem.* 269: 26267–26273.
52. Pavlakis, G. N. and Hamer, D. H. 1983. Regulation of a metallothinein-growth hormone hybrid gene in bovine papilloma virus. *Proc. Natl. Acad. Sci., U.S.A.* 80: 397–401.
53. Mostov, K. E. and Dietcher, D. L. 1986. Polymeric immunoglobulin receptor expressed in MDCK cells transcytosis IgA. *Cell* 46: 613–621.
54. Mostov, K. E. 1994. Transepithelial transport of immunoglobulins. *Annu. Rev. Immunol.* 12: 63–84.
55. Breitfield, P. P., McKinnon, W. C., and Mostov, K. E. 1990. Effect of nocodazole on vesicular traffic to the apical and basolateral surfaces of polarized MDCK cells. *J. Cell. Biol.* 111: 2365–2373.
56. Nagura, H., Nakane, P. K., and Brown, W. R. 1979. Translocation of dimeric IgA through neoplastic colon cells in vitro. *J. Immunol.* 123: 2359–2368.
57. Musil, L. S. and Baenziger, J. U. 1987. Cleavage of membrane secretory component to soluble secretory component occurs at the cell surface of rat hepatocyte monolayers. *J. Cell. Biol.* 104: 1725–1733.
58. Moritz, D. and Groner, B. 1995. A spacer region between the single chain antibody and the CD3ξ-chain domain of the chimeric T cell receptor components is required for efficient ligand binding and signaling activity. *Gene Ther.* 2: 539–546.
59. Konstan, M. W., Hilliard, K. A., Norvell, T. M., and Berger, M. 1994. Bronchoalveolar lavage findings in cystic fibrosis patients with stable, clinically mild lung disease suggest ongoing infection and inflammation. *Am. Rev. Respir. Crit. Care Med.* 150: 448–454.
60. Ferkol, T., Mularo, F., Hilliard, J., Lodish, L., Perales, J. C., Ziady, A. G., and Konstan, M. W. Transfer of the gene encoding human alpha$_1$ antitrypsin into pulmonary alveolar macrophages via the mannose receptor. Submitted for publication.
61. Travis, J. 1988. Structure, function, and control of neutrophil proteinase. *Am. J. Med.* 84: 37–42.
62. Stetler, G., Brewer, M. T., and Thompson, R. C. 1986. Isolation and sequence of a gene encoding a potent inhibitor of leukocyte proteases. *Nucleic Acids Res.* 14: 7883–7896.
63. Glockshuber, R., Malia, M., Pfitzinger, I., and Pluckthun, A. 1990. A comparison of strategies to stabilize immunoglobulin Fv fragments. *Biochemistry.* 29: 1362–1367.
64. Prasher, D. C., Eckenrode, V. K., Ward, W. W., Prendergast, F. G., and Cormier, M. J. 1992. Primary structure of the *Aequorea Victoria* green fluorescent protein. *Gene.* 111: 229–233.
65. Inouye, S. And Tsuji, F. I. 1994. Aequorea green fluorescent protein: expression of the gene and fluorescent characteristics of the recombinant protein. *FEBS Letters.* 341: 277–280.
66. Flach, J., Bossie, M., Vogel, J., Corbett, A., Jinks, T., Willins, D. A., and Silver, P. A. 1994. A yeast RNA-binding protein shuttles between the nucleus and cytoplasm. *Mol. Cell. Biol.* 14: 8399–8407.
67. Bian, J., Lin, X., and Tang, J. 1995. Nuclear localization of HIV-1 matrix protein P17: the use of *A. victoria* GFP in protei tagging and tracing. *FASEB J.* 9: A1279 (Abstract).
68. Wang, S. And Hazelrigg, T. 1994. Implications for bcd MRNA localization from spatial distribution of exu protein in Drosophila oogenesis. *Nature.* 369: 400–403.
69. Loman, S, Radl, J., Jansen, H. M., Out, T. A., and Lutter, R. 1997. Vectorial transcytosis of dimeric IgA by the Calu-3 human lung epithelial cell line: upregulation by IFN-γ. *Am. J. Physiol.* 272 (Lung Cell Mol. Physiol.): L951–L958.
70. Kvale, D., Lovhaug, D., Sollid, M., and Brandtzaeg, P. 1988. Tumor necrosis factor-α upregulates expressionof secretory component, the epithelial receptor for polymeric Ig. *J. Immunol.* 140: 3086–3089.
71. Phillips, J. O., Everson, M. P., Moldoveanu, Z., Lue, C., and J. Mestecky. 1990. Synergistic effect of IL-4 and INF-γ on the expression of polymeric Ig receptor (secretory component) and IgA binding by human epithelial cells. *J. Immunol.* 145: 1740–1744.
72. Balough, K., McCubbin, M., Weinberger, M., Smits, W., Ahrens, R., and Fick, R. 1995. The relationship between infection and inflammation in the early stages of lung disease from cystic fibrosis. *Pediatr. Pulmonol.* 20: 63–70.
73. Pier, G. B., Small, G. J., and Warren, H. B. 1990. Protection against mucoid *Pseudomonas aeruginosa* in rodent models of endobronchial infections. *Science* 249: 537–540.
74. Konstan, M. W., Vargo, K. M., and Davis, P. B. 1990. Ibuprofen attenuates the inflammatory response to *Pseudomonas aeruginosa* in a rat model of chronic pulmonary infection: Implications for antiinflammatory therapy in cystic fibrosis. *Am.Rev.Respir.Dis.* 141: 186–192.
75. Cash, H. A., Woods, D. E., McCullough, B., Johanson, W. G., and Bass, J. A. 1979. A rat model of chronic pulmonary infection with *Pseudomonas aeruginosa Am. Rev. Respir. Dis* 119: 453–459.
76. Rennard, S. I., Basset, G., Lecossier, D., O'Donnell, K. M., Pinkston, P., Martin, P. G., and Crystal, R. G. 1986. Estimation of volume of epithelial lining fluid recovered by lavage using urea as a marker of dilution. *J. Appl. Physiol.* 60: 532–538.
77. Bolender, R. P., Hyde, D. M., and Dehoff, R. T. 1993. Lung morphometry: A new generation of tools and experiments for organ, tissue, cell, and molecular biology. *Am. J. Physiol.* 265 (Lung Cell. Mol. Physiol.): L521–L548.
78. van Heeckeren, A., Ferkol, T., Zakem-Cloud, H., Hamedani, A., Mularo, F., Konstan, M., and Tosi, M. Effects of bronchopulmonary inflammation induced by *Pseudomonas* on adenovirus-mediated gene transfer to airway cells in mice. *Gene Ther.* Accepted for publication.

We claim:

1. A fusion protein comprising a single chain Fv molecule directed against a transcytotic receptor covalently linked to a therapeutic protein.

2. The fusion protein of claim 1 wherein the transcytotic receptor is human secretory component of polymeric immunoglobulin receptor.

3. The fusion protein of claim 2 wherein the therapeutic protein is $\alpha_1$-antitrypsin.

4. The fusion protein of claim 2 wherein the therapeutic protein is a cytokine.

5. The fusion protein of claim 4 wherein the therapeutic protein is interleukin-2.

6. The fusion protein of claim 4 wherein the therapeutic protein is interleukin-10.

7. The fusion protein of claim 2 wherein the therapeutic protein is a peptide antibiotic.

8. The fusion protein of claim 1 further comprising a linker region of not more than 30 amino acid residues covalently linked to and between the single chain Fv molecule and the therapeutic protein.

9. The fusion protein of claim 2 wherein the therapeutic protein is SLPI.

10. The fusion protein of claim 2 wherein the therapeutic protein is a defensin.

11. The fusion protein of claim 2 wherein the therapeutic protein is a protegrin.

* * * * *